United States Patent [19]

Niederhauser

[11] Patent Number: 4,978,341
[45] Date of Patent: Dec. 18, 1990

[54] INTRODUCER VALVE FOR A CATHETER ARRANGEMENT

[75] Inventor: Werner Niederhauser, Zurich, Switzerland

[73] Assignee: Schneider Europe, Zurich, Switzerland

[21] Appl. No.: 334,626

[22] Filed: Apr. 6, 1989

[30] Foreign Application Priority Data

Apr. 7, 1988 [CH] Switzerland .................. 1278/88

[51] Int. Cl.$^5$ .................................. A61M 29/02
[52] U.S. Cl. ............................. 604/167; 604/169
[58] Field of Search ............. 604/167, 169, 256, 53

[56] References Cited

U.S. PATENT DOCUMENTS

| | | | |
|---|---|---|---|
| 4,243,034 | 1/1981 | Brandt | 604/169 |
| 4,475,548 | 10/1984 | Muto | 604/167 |
| 4,634,433 | 1/1987 | Osborne | 604/163 |
| 4,723,550 | 2/1988 | Bales et al. | |
| 4,817,631 | 4/1989 | Schnepp-Pesch et al. | 604/167 |

FOREIGN PATENT DOCUMENTS

| | | | |
|---|---|---|---|
| 0223451 | 5/1987 | European Pat. Off. | 604/167 |
| 3042229 | 5/1982 | Fed. Rep. of Germany | 604/167 |

*Primary Examiner*—John D. Yasko
*Assistant Examiner*—Anthony M. Gutowski
*Attorney, Agent, or Firm*—Peter C. Richardson; Roger C. Turner; Thomas C. Naber

[57] ABSTRACT

An introducer valve has a connecting housing enclosing a generally cylindrical elastomeric valve body having a proximal end, a distal end, a central axis, and a central longitudinal opening. The central opening has a proximal aperture tapering inwardly to the central axis and has a distal aperture tapering inwardly to the central axis, and is adapted to receive an elongated guidewire or catheter element. The valve body has an exterior surface which tapers from the proximal end inwardly and from the distal end inwardly generally parallel with the respective apertures (in a somewhat hourglass configuration). The central opening of the valve body is normally sealed closed, and further surrounds and seals a penetrating catheter which is introduced or changed within the valve. The valve further comprises an elastomeric ring which circumscribes the center of the valve body. This ring facilitates the compressive sealing of the central opening and particularly facilitates liquid-tight sealing with penetrating elements having greatly differing diameters of about 1 mm to about 6 mm.

2 Claims, 1 Drawing Sheet

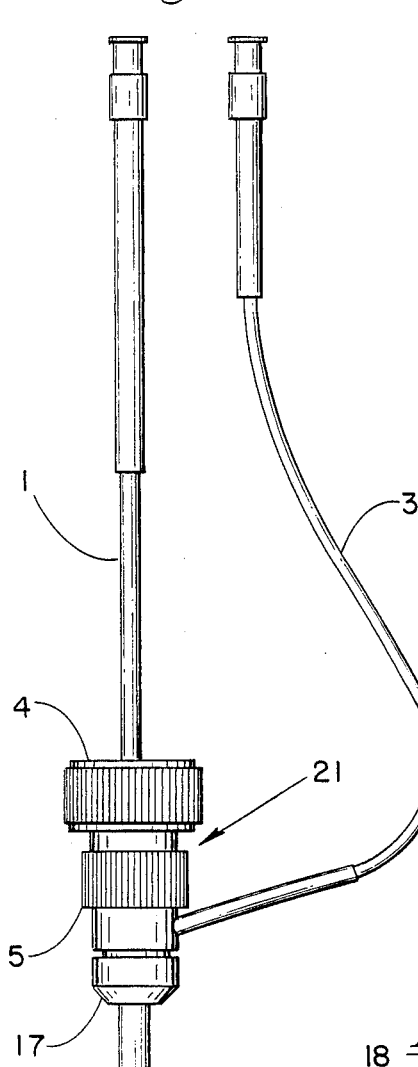
Fig.-1
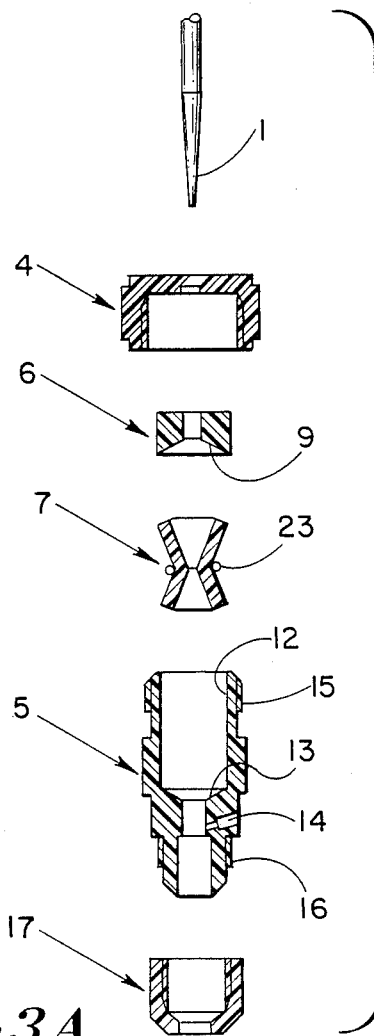
Fig.-2
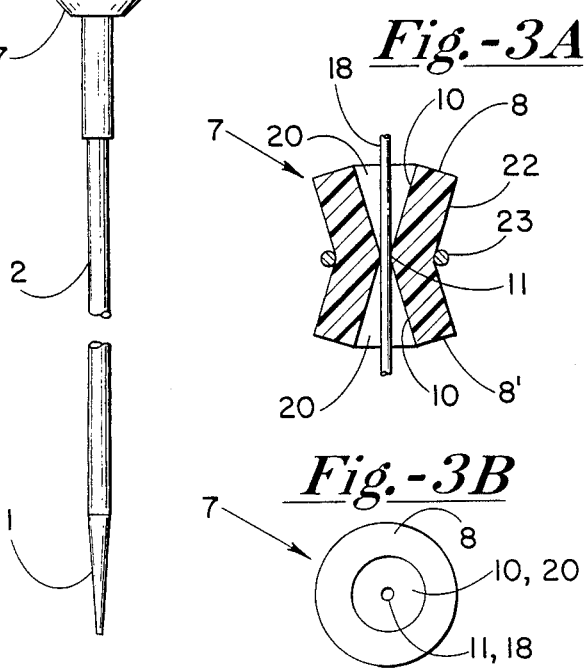
Fig.-3A
Fig.-3B
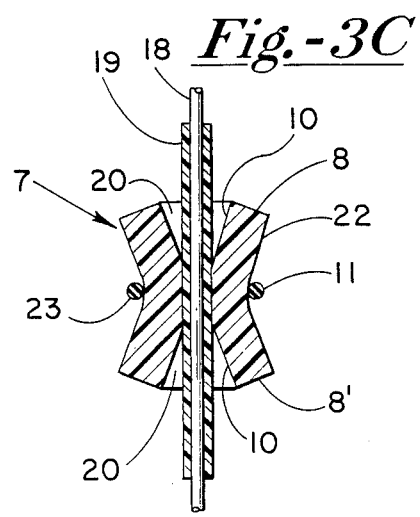
Fig.-3C

INTRODUCER VALVE FOR A CATHETER ARRANGEMENT

BACKGROUND OF THE INVENTION

The invention relates to a valve for introducing a guidewire, dilator, or catheter into a vessel of a patient while maintaining a liquid seal at all times.

An introducer valve of the prior art is known in which an O-ring of silicon rubber is enclosed in a housing through which a carrier tube of a catheter is inserted for the purpose of providing a liquid-tight seal. In another known tube connecting introducer valve, there is similarly arranged a radial seal which surrounds an elongated guide element, which is substantially thinner than the carrier tube, for the purpose of providing a pressure-tight seal. Also known, is an introducer valve having several flat sealing elements arranged one behind the other with different sized openings. In this stated arrangement, each sealing element is tailored to a certain diameter such that only one of these surrounding elements seals the elongated element which is inserted through the valve.

In practice, these valves often prove not to be liquid-tight. These prior art sealing elements also demand a high level of precision to fabricate and assemble and therefore are relatively expensive to manufacture.

SUMMARY OF THE INVENTION

The object of the present invention is to provide an introducer valve which reliably seals penetrating elements of substantially different diameters, and which also can be manufactured inexpensively.

This object is achieved by the present invention in which an introducer valve has a connecting housing enclosing a generally cylindrical elastomeric valve body having a proximal end, a distal end, a central axis, and a central longitudinal opening. The central opening has a proximal aperture tapering inwardly to the central axis and has a distal aperture tapering inwardly to the central axis, and is adapted to receive an elongated guidewire or catheter element. In a first embodiment, the valve body preferably has an exterior surface which tapers from the proximal end inwardly and from the distal end inwardly generally parallel with the respective apertures (in a somewhat hourglass configuration). The central opening of the valve body is normally sealed closed, and further surrounds and seals a penetrating catheter which is introduced or changed within the valve.

In a second embodiment, the valve further comprises an elastomeric ring which circumscribes the center of the valve body. This ring facilitates the compressive sealing of the central opening and particularly facilitates liquid-tight sealing with penetrating elements having greatly differing diameters of about 1 mm to about 6 mm.

Since the introducer valve of the present invention has only one sealing element, the assembly is substantially easier and more reliably accomplished than with multiple elements of the prior art valves. The valve is advantageous in that the seal is formed with penetrating guides and catheters ranging from about 1 mm to about 6 mm in a continuous and self-adjusting manner and the penetrating elements can be inserted using relatively very little force.

BRIEF DESCRIPTION OF THE DRAWINGS

Further characteristics and advantages of the invention will become apparent from the description of preferred, but not exclusive, embodiments of the invention, given only by way of nonlimitative examples, which make reference to the accompanying drawings in which:

FIG. 1 is a side elevational view of the introducer valve and catheter arrangement;

FIG. 2 is an exploded longitudinal sectional view of FIG. 1 illustrating the internal components of the valve;

FIG. 3a is an enlarged view of the valve body of FIG. 2 further including an inserted small guidewire;

FIG. 3b is a top plan view of the valve body illustrated in FIG. 3a; and

FIG. 3c is similar to FIG. 3a further illustrating a catheter inserted through the valve body of the present invention.

DETAILED DESCRIPTION OF THE INVENTION

As shown in the figures, the valve and catheter arrangement has a tube connecting housing 21 which has an introduction tube 2 fixed thereto typically by means of a union nut 17 and which allows the introduction of a guidewire 18 (see FIGS. 3a and 3b), into the vessel of the patient. The tube connecting housing 21 has a cylindrical enclosure 5 having a longitudinal passageway 12 which is circular in cross-section. An elastomeric sealing element is provided by installing a valve body 7 within enclosure 5 which is retained by a casing 6 and secured at the proximal end by an end cap 4. The enclosure 5 includes a lateral passage 14 communicating with passageway 12 and which has a tube 3 extending from the passage 14 to provide secondary access to the central passageway, for example, for actuating an expansion balloon connected to a suction and pressure pump.

As shown, (particularly in FIG. 3a), the valve body 7 has a proximal end 8, a distal end 8' and a central longitudinal passageway 20. The longitudinal passageway 20 includes a proximal aperture tapering inwardly to the central axis and has a distal aperture tapering inwardly to the central axis which form generally conical surfaces 10 at each end interconnected by a 1 mm central passage along the central axis. A conical aperture tapered at an angle of about 20° relative to the central longitudinal axis was found to be quite suitable. The narrowest point 11 along the central passageway 20 is about 1 mm in diameter in the free preinstalled condition. The exterior surface 22 of valve body 7 is also tapered inwardly from the proximal and distal ends and are essentially parallel to the respective inner surfaces 10, (in a somewhat hourglass configuration) such that the valve body 7 has generally uniform wall thickness. The proximal and distal ends of valve body 7 are generally perpendicular to the respective inner surfaces thereby forming generally frustoconically shaped end surfaces 8 and 8'. The valve body 7 is preferably formed of silicon rubber having a shore hardness of about 20 to 40 and more preferably of about 20. The valve body can of course be molded from a variety of other elastomeric materials.

The length of the valve body 7 and the length of the passageway 12 within enclosure 5 are configured to snugly engage the valve body 7 within the housing 21. The passageway 12 includes an inward shoulder 13 adapted to engage the distal end 8', and the casing 6 includes a surface 9 adapted to engage the proximal end 8 of the valve body 7 when the end cap 4 is secured. The installation of the valve body 7 into the housing enclosure 5 tends to naturally compress the body to further facilitate the sealing action of the valve.

Referring particularly to FIGS. 3a and 3c, as a penetrating element such as guidewire 18 is inserted into the valve body, the central area expands resulting in a wide contact surface between the valve body and the guidewire providing a reliable liquid-tight seal. As a substantially larger diameter tube 19 (FIG. 3c) for example having a diameter of 6 mm, is pushed onto guidewire 18, then a comparatively wider contact surface results at 11 between valve body 7 and the tube 19 which expands radially outward. Since the valve body 7 is supported only at the distal end 8' and the proximal end 8, it can be displaced in the central area without generating high radial forces and with controlled deformation. The comparatively thick tube 19 can therefore be shifted in the longitudinal direction with little friction or resistance from the valve body 7.

The valve body 7 is preferably symmetrical in relation to its longitudinal axis, to exert equal push and pull forces upon the catheter and to ensure that the valve body cannot be incorrectly assembled. However, special circumstances may require that the apertures have different angles and do not converge at the center of the valve body.

A further or second embodiment is also illustrated by referring to FIGS. 3a and 3c in which the valve body of the first embodiment is enhanced by the addition of an elastomeric ring 23 which circumscribes the exterior surface of the valve body. The elastomeric ring 23 is particularly useful in procedures requiring penetrating elements having greatly differing diameters. Experiments have shown that it is possible to avoid cracks forming in the valve body 7 having the ring, even under very heavy stresses and radial expansion of up to 400 percent. The ring can be made of silicon rubber and circumscribe valve body 7 as illustrated at its narrowest central point. The ring supports the immediate contraction of the valve body to seal the valve when the catheter is being changed. The elastomeric ring is particularly advantageous in that the valve body 7 can be manufactured from less elastic materials such as polyurethane, in which case the elastomeric ring facilitates the sealing action of the valve body.

The foregoing embodiments provide examples of an introducer valve which operates reliably with various sized penetrating elements. The valve is relatively easy to fabricate and reliable to assemble and is thus extremely cost-effective.

I claim:

1. An introducer valve body, for use within a connecting housing having a longitudinal passageway, for sealing the passageway and for sealing an elongated guidewire or catheter element which may be inserted within the passageway, comprising:

a generally cylindrical elastomeric body having a proximal end, a distal end, a central axis and a central longitudinal opening therein, and further comprising an elastomeric ring which circumscribes the valve body to facilitate the sealing of the valve;

said opening having a proximal aperture tapering inwardly to the central axis and having a distal aperture tapering inwardly to the central axis, and adapted to receive the elongated element, and wherein the exterior surface of the body tapers inwardly from said proximal end and tapers inwardly from said distal end generally parallel respectively with said proximal and distal apertures.

2. The introducer valve body of claim 1 where said ring is positioned to circumscribe the center of said body.

* * * * *